United States Patent [19]

Chornenky et al.

[11] Patent Number: 5,925,016
[45] Date of Patent: Jul. 20, 1999

[54] SYSTEMS AND METHODS FOR DRUG DELIVERY INCLUDING TREATING THROMBOSIS BY DRIVING A DRUG OR LYTIC AGENT THROUGH THE THROMBUS BY PRESSURE

[75] Inventors: Victor I. Chornenky, Minnetonka; Michael R. Forman, St. Paul, both of Minn.

[73] Assignee: XRT Corp., St. Paul, Minn.

[21] Appl. No.: 08/534,856

[22] Filed: Sep. 27, 1995

[51] Int. Cl.$^6$ .................................................. A61M 29/00
[52] U.S. Cl. .................................. 604/96; 604/19; 604/35; 604/101
[58] Field of Search ................................. 604/53, 27, 28, 604/101, 102, 35, 43, 96, 95, 19

[56] References Cited

U.S. PATENT DOCUMENTS

| | | |
|---|---|---|
| 4,573,966 | 3/1986 | Weikl et al. . |
| 4,883,459 | 11/1989 | Calderon ............................. 604/101 X |
| 5,261,877 | 11/1993 | Fine et al. . |
| 5,342,306 | 8/1994 | Don Michael ........................ 604/53 X |
| 5,376,083 | 12/1994 | Mische . |
| 5,419,763 | 5/1995 | Hildebrand ............................ 604/101 X |
| 5,453,090 | 9/1995 | Martinez et al. ........................... 604/53 |
| 5,484,412 | 1/1996 | Pierpont ............................... 604/102 X |
| 5,620,604 | 4/1997 | Stone .................................... 604/28 X |
| 5,626,601 | 5/1997 | Gershony et al. ..................... 604/96 X |

OTHER PUBLICATIONS

Dependence of Blood Clot Lysis on the Mode of Transport of Urokinase into the Clot—A Magnetic Resonance Imaging Study in Vitro, Blinc et al., Thrombosis and Haemostasis 65 (5): 549–552, 1991.

Pressure and Volume Control for Local Drug–Delivery Catheters: Development of a New Microprocessor–controlled System, Lambert et al., Coronary Artery Disease, vol. 5, No. 2, pp. 163–167, 1994.

Local Drug Delivery Catheters: Functional Comparison of Porous and Microporous Designs, Lambert et al., Coronary Artery Disease, vol. 4, No. 5, pp. 469–475, 1993.

*Primary Examiner*—Wynn Wood Coggins
*Assistant Examiner*—N. Kent Gring
*Attorney, Agent, or Firm*—Merchant & Gould P.C.

[57] ABSTRACT

Systems and methods for treating thrombosis by driving the drugs or lytic agents through the thrombus by pressure, are disclosed. The system preferably comprises a guide catheter with an occlusion balloon for isolating the region proximal to the thrombus, a guide wire with an occlusion balloon for isolating the region distal to the thrombus and an infusion catheter for delivering drugs or other agents into the region distal to the thrombus under pressure. A lumen of the guide catheter is preferably provided to evacuate material proximal to the thrombus, decreasing the pressure in the proximal to the thrombus. The lumen can be coupled to a thrombus filter to remove thrombolytic material from the drug or lytic agent evacuated from the proximal region. The filtered drug or lytic agent can then be redelivered into the distal region. Recycling of the drug or lytic agent in this manner decreases the costs of the procedure. The systems and methods of the invention can be used to treat other blockages in lumens or vessels in the body or to deliver drugs or other agents to lumens, vessels or cavities within the body, as well.

8 Claims, 6 Drawing Sheets

FIG. 12

SYSTEMS AND METHODS FOR DRUG DELIVERY INCLUDING TREATING THROMBOSIS BY DRIVING A DRUG OR LYTIC AGENT THROUGH THE THROMBUS BY PRESSURE

FIELD OF THE INVENTION

Systems and methods for treating thrombosis in the cardiovascular system and, more particularly, a system for enhancing the activity of a drug or lytic agent on a thrombus by driving the drug or lytic agent through the thrombus by the pressure of the drug delivery. The systems and methods of the present invention can also be used to deliver drugs or other agents for other purposes and to other regions of the body, as well.

BACKGROUND OF THE INVENTION

Thrombosis, the formation of a clot or thrombus in the cardiovascular system from the constituents of blood, is a potentially life threatening condition. Thrombosis can develop in any part of the cardiovascular system, but is most common in veins, particularly the deep veins in the leg. Thrombosis can result from a variety of causes including poor circulation, trauma, prolonged bed rest, or hip surgery, for example. In the arteries, thrombosis can be caused by arteriosclerosis. Thrombosis can develop in cerebral vessels, as well.

If a portion of the thrombus separates and is transported through the cardiovascular system, it can cause an embolism, or blockage of a blood vessel. A thrombus in a deep vein in the leg can cause a pulmonary embolism. A thrombus in a coronary artery can cause myocardial infarction. Similarly, a thrombus in a cerebral artery can cause cerebral infarction.

During the early development of thrombosis, up to about seven days, the thrombus is soft and can be treated by a variety of techniques. Application of urokinase to a clot under pressure has shown improved results over diffusion. Blinc, A., et al., "Dependance of Blood Clot Lysis on the Mode of Transport of Urokinase into the Clot—A Magnetic Resonance Imaging Study In Vitro," Thrombosis and Haemostasis, 65(5) 549–552 (1991). A pulse spray of urokinase has been directed onto soft thrombi to mechanically break up and dissolve it. High pressure water has also been directed onto the thrombus to destroy it. The thrombus can also be broken by a laser or a drill. The broken or dislodged portions of the thrombus are aspirated through a catheter so that they cannot migrate and obstruct other vessels of the cardiovascular system. Results have been mixed, with some treatments damaging tissue, causing another thrombotic or stenotic process. A surgical procedure may be required to remove the thrombus, as well.

Drug delivery in the cardiovascular system is also used to prevent restenosis percutaneous transluminal coronary angioplasty (PTCA) and percutaneous transluminal angioplasty (PTA). Drugs and other agents are delivered to lumens, vessels and cavities in other portions of the body, such as the urethra, bladder, prostate, rectum, bile duct, pancreatic duct and central nervous system, such as along the spinal column, to treat a variety of conditions, as well.

SUMMARY OF THE INVENTION

The present invention provides systems and methods for the delivery of drugs or agents into lumens, vessels or cavities of the body. The systems and methods of the present invention can also be used to force a drug or agent through a blockage or occlusion, such as a thrombus or tumor, in a lumen, vessel or cavity. The present invention also enables the evacuation, filtration and redelivery of the drug or agent.

In accordance with one embodiment of the present invention, a system for treating thrombosis is disclosed comprising a pump and a guide catheter comprising a shaft with a distal and proximal portion, and an occlusion balloon coupled to the distal portion of the shaft. A first lumen extends longitudinally through the shaft, coupled to the pump such that material can be evacuated through the second lumen by the pump. A second lumen extends longitudinally through the shaft to a port in fluid communication with the occlusion balloon.

The system further comprises a guide wire comprising a proximal portion and a distal portion, an occlusion balloon coupled to the distal portion of the guide wire, and a lumen extending longitudinally through the guide wire to a port providing fluid communication between the lumen and the occlusion balloon.

The system further comprises an infusion catheter comprising a shaft with a proximal portion and a distal portion. An infusion lumen extends longitudinally through the shaft to a port in the distal portion of the shaft, providing fluid communication between the infusion lumen and the exterior of the shaft.

The above system can be used to deliver drugs or other agents to lumens, vessels or cavities of the body, as well.

In accordance with another embodiment of the invention, a system for treating a blockage in a lumen vessel is disclosed comprising means for delivering a drug or other agent to a first region proximate the blockage and means for forcing the drug or other agent from the first region through the thrombus.

A system for treating thrombosis is also disclosed comprising at least one inflation/deflation unit and a first occlusion balloon coupled to the inflation/deflation unit, such that the first occlusion balloon can isolate a region distal to a thrombus. A second occlusion balloon is coupled to the inflation/deflation unit, such that the second occlusion balloon can isolate a second region proximal to the thrombus.

A pump and a first lumen are coupled to the first region. A drug or lytic agent can be infused into the first region through the first lumen under pressure by the pump, to force the drug or other agent through the thrombus.

A second lumen is coupled to the pump and the second region such that material can be evacuated from the second region. A filter is provided between the second lumen and the pump, such that material evacuated from the second region is filtered prior to infusion into the first region through the first lumen.

A kit is also disclosed comprising a guide catheter with an occlusion balloon coupled to its distal portion, and a guide wire with an occlusion balloon coupled to its distal portion, in a sterile package. An infusion catheter may be included in the kit, as well.

In accordance with another embodiment of the present invention, an infusion catheter is disclosed comprising a shaft and a first lumen extending longitudinally through the shaft to a first port for infusing drugs or other agents. A second lumen extends longitudinally through the shaft to a second port proximal to the first port, for evacuating material. A first occlusion balloon is coupled to the shaft, distal to the second port. A third lumen extends longitudinally through the shaft to a third port for providing inflation fluid to the first occlusion balloon.

In another embodiment of the invention, a method of treating a blockage in a lumen or vessel is disclosed comprising delivering a drug or other agent to a first region proximate the blockage and forcing the drug or other agent from the first region through the blockage.

A method of treating thrombosis is also disclosed comprising occluding a first region proximate a first side of a thrombus, occluding a second region proximate a second side of the thrombus, delivering a drug or other agent to the first region, forcing the drug or other agent through the thrombus into the second region, evacuating the drug or other agent from the second region, filtering the evacuated drug or agent and delivering the filtered drug or other agent distal to the thrombus.

DESCRIPTION OF THE INVENTION

Figure 1:
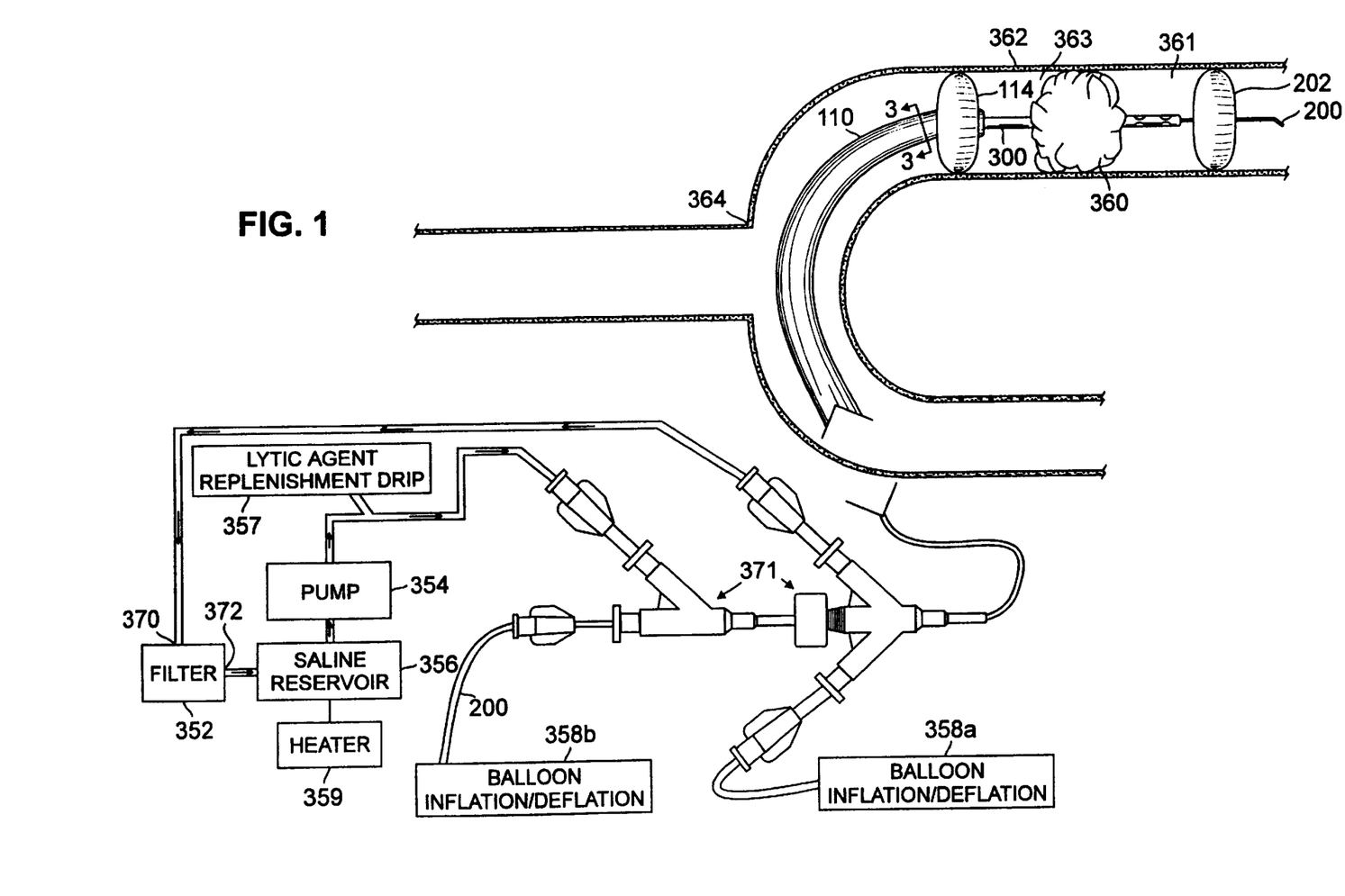
FIG. 1 illustrates one embodiment of the system of the present invention.

FIG. 1 shows a system for treating deep vein thrombosis in accordance with one embodiment of the present invention. The system comprises a guide catheter 110 with an occlusion balloon 114 proximate its distal end, a guide wire 200, which preferably includes an occlusion balloon 202 proximate its distal end, and an infusion catheter 300. A thrombus filter 352, a pump 354 and a saline reservoir 356 are preferably coupled to the guide catheter 110 and infusion catheter 300, as described further, below. A drip 357 of drug or other agent, for example, may be coupled to the infusion catheter 300. Instead of the drip 357, the drug or lytic agent can be added to the saline reservoir 356. A heater 359 is preferably coupled to the saline reservoir 356. Also shown in FIG. 1 are balloon inflation/deflation units 358a, 358b, which are coupled to the guide catheter 110 and guide wire 200, respectively. A thrombus 360 is shown in the femoral vein 362. The guide catheter 110 has been inserted contralaterally and advanced across the femoral arch 364. The external portions of the system are coupled to the proper lumens through Touhy-Borst or other such connectors 371, as is known in the art.

The term "lytic agent" will generally be used hereafter to refer to any drug or agent which can dissolve a thrombus. Such lytic agents include urokinase, streptokinase and recombinant tissue plasminogen activator (rTPA), for example.

A preferred guide catheter 110 for use in the present invention is described and claimed in U.S. patent application entitled "Guide Catheter With An Occlusion Balloon" (Attorney Docket No. 22406.10), filed on the same day as the present application and assigned to the same assignee as the present application. That application is incorporated by reference herein.

Figure 2:
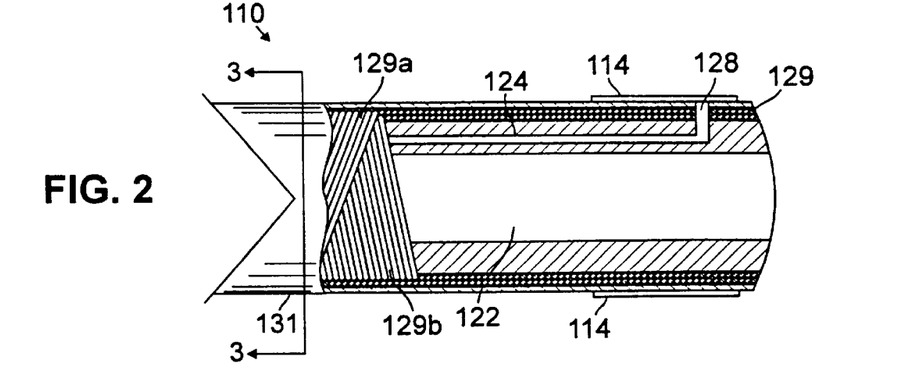
FIG. 2 is a partially sectioned view of a guide catheter for use in the systems and methods of the present invention.
Figures 3, 4A, 4B:
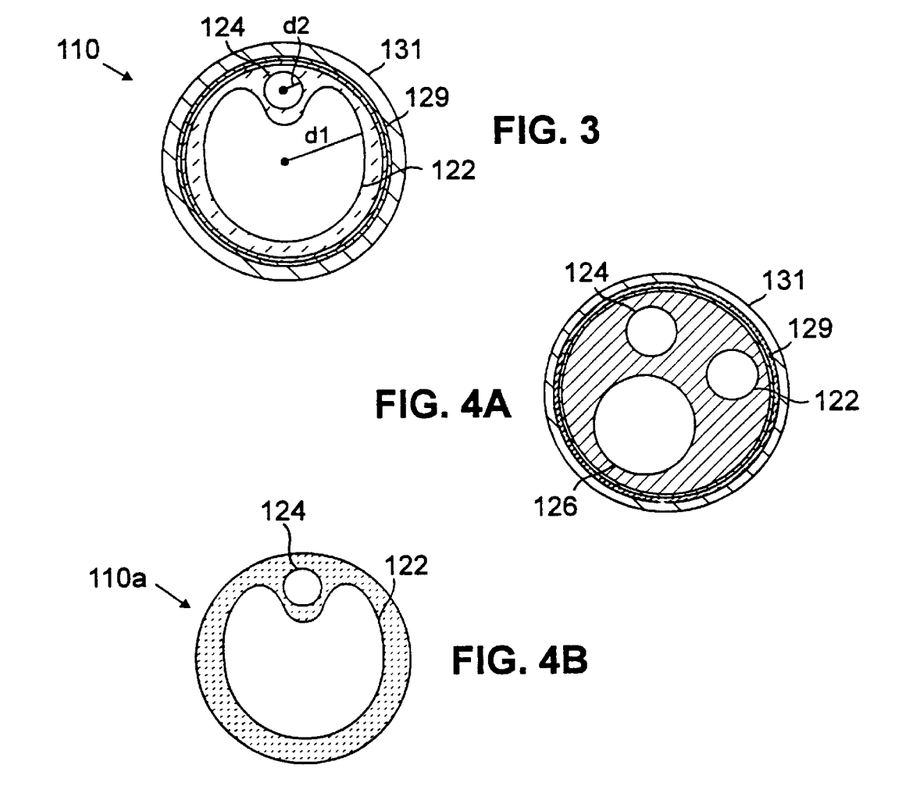
FIG. 3 is a cross sectional view along line 3—of the guide catheter of FIG. 2.
FIG. 4A is a cross sectional view of another embodiment of a guide catheter for use in the present invention.
FIG. 4B is a cross sectional view of a single layer embodiment of the guide catheter which can be used in the present invention.

FIG. 2 is a partially sectioned view of the preferred guide catheter 110 of FIG. 1, with the infusion catheter 300 and guide wire 200 removed. FIG. 3 is a cross sectional view of the guide catheter 110 along line 3—3 of FIG. 1. The guide catheter 110 preferably comprises a first lumen 122 for accommodating the guide wire 200 and the infusion catheter 300, which extends longitudinally through the guide catheter 110. Dislodged and dissolved thrombolytic material is preferably evacuated through the first lumen 122, as described further below. A second lumen 124 extends longitudinally through the guide catheter 110 for providing inflation fluid to the occlusion balloon 114. The distal portion of the second lumen 124 is sealed or closed. A port 128 is provided through the walls of the guide catheter 110, to the second lumen 124, to provide fluid communication between the second lumen 124 and the occlusion balloon 104. Alternatively, a third lumen 126 can be provided for evacuation of thrombolytic material, as shown in the cross sectional view of FIG. 4.

The guide catheter 110 also preferably comprises a braid 129 of stainless steel or Kevlar®, as is known in the art, to prevent the guide catheter 110 from kinking as it is advanced through an artery or vein, over the guide wire, to the site of interest. The braid 129 also improves the pushability and torqueability of the guide catheter 110.

Figure 5:
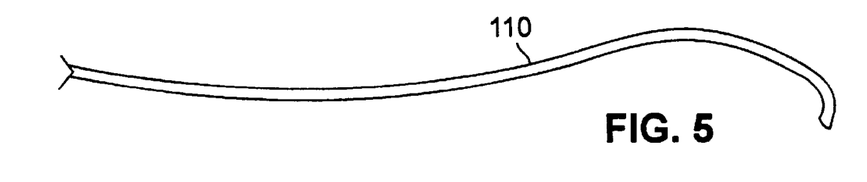
FIG. 5 is a side view of the guide catheter for use in the present invention.

A layer of polymeric material 131 is provided over the braid 129 to protect vessel walls and to provide a unitary structure and support. The outer layer 131 can be polyethylene, nylon, a blend of polyether block amide (PEBA) and nylon, or polyurethane, for example. The distal portion of the guide catheter 110 is preferably curved to ease traversal of the femoral arch 362, shown in FIG. 1. A standard right Judkins tip may be used, as shown in FIG. 5. Other tip configurations may be used, as well, depending on the site of the procedure and preference of the doctor.

The material in the distal portion of the guide catheter 110 is preferably loaded with a radiopaque powder such as bismuth or barium to enable tracking of the guide catheter 110 on a fluoroscope during a procedure. Radiopaque bands of gold or tantalum, for example, may also be used.

A 10 French guide catheter (outer diameter 0.130 inches, inner diameter 0.105 inches) is appropriate for deep vein applications. Other sizes of guide catheter can be used, as well, depending on the diameter of the site of interest and preference of the doctor. Preferably, in a 10 French guide catheter, the first lumen 122 for accommodating the guide wire 200 and infusion catheter 300 has a diameter d1 of about 0.100 inches and the second, inflation lumen 124 has a diameter d2 of about 0.010 inches. In this embodiment, the first lumen 122 must be large enough to accommodate the infusion catheter 300 and to evacuate material.

Preferably, two layers of braid 129a, 129b are provided wound with opposite pitch. Each braid layer typically has a thickness of about 0.001–0.003 inches. The total thickness of the braid layers is then about 0.002–0.006 inches. The outer polymeric layer 131 is about 0.002–0.005 inches.

The guide catheter 110 can be manufactured by extruding a multilumen shaft comprising the first lumen 122 and the second lumen 124, in a multilumen extrusion process, as is known in the art. Additional lumens can be provided, as well. The shaft can then be braided with the two layers of stainless steel or Kevlar®, for example, also as is known in the art, preferably with opposite pitch. A polymer can then be extruded over the braid.

The multilumen shaft is preferably high or low density polyethylene which has a low friction surface easing passage of the guide wire 200 and infusion catheter 300. Polyurethane fluorinated copolymer of ethylene propylene (FEP), polyether block amide, nylon 12, polyamide, polyamide copolymer, polypropylene, polyester copolymer, polyvinyl difluoride or silicon rubber can also be used. The outer diameter of the multilumen shaft is about 0.105 inches. The outer layer can be polyethylene or polyurethane, and is preferably thin. The thickness of the outer layer can be about 0.010 inches, for example. The first lumen 122 and second lumen 124 preferably have the dimensions described above.

The port 128 can be drilled or otherwise formed through the outer wall of the multilumen shaft to the second, inflation lumen 124 to enable the passage of inflation fluid through the walls of the guide catheter 110. The occlusion balloon 114 can be attached to the guide catheter 110 over the port 128 by thermal bonding or an adhesive, such as cyanoacrylic adhesives, ultraviolet activated adhesives or epoxies, as is known in the art. The balloon 114 can be any soft, non-thrombogenic material known in the art, such as polyamide, polyamide copolymer, polyethylene, PEBAX®, nylon, Kraton®, silicone, and C-Flex™, which is a blend of polyurethane and silicone available from Polymer Technologies, Inc., Florida, for example.

The outer diameter of the occlusion balloon 114 when fully inflated should be sufficiently greater than the diameter of the vessel that the balloon sufficiently bears against the vessel walls to prevent the passage of fluid or material. If the diameter of the portion of the vein obstructed by the thrombus is about 6.0 mm, for example, the outer diameter of an inflated balloon 114 is preferably about 6.1 mm. The length of the balloon is preferably between about 1–2 cm.

The guide catheter 110 is preferably coated with a lubricous material such as silicone, to ease passage through a vein or artery.

The guide catheter 110 can also be formed of a commercially available guide catheter, such as the Softip® available from Schneider (USA), Inc., Minneapolis, Minn., the Cordis Brite Tip®, available from Cordis Corporation, Murray Hill, N.J., Sherpa from Medtronic, Inc., Minneapolis, Minn. The Schneider Softip® comprises an inner layer of Teflon®, a stainless steel braid and an outer layer of polyethylene or polyurethane. The Cordis Brite Tip® comprises Duralyn® and two braids of stainless steel, a stiff braid on the body and a less stiff braid in the distal portion of the catheter.

A multilumen shaft of polyethylene, preferably comprising the first lumen 122 and the second lumen 124, can be inserted into the lumen of any of the commercial guide catheters mentioned above, or other commercial guide catheters. The shaft can be formed by a multilumen extrusion process of the materials discussed above. The shaft can then be bonded to the lumen of the guide catheter by an adhesive or thermal bonding. As above, a third lumen can alternatively be provided for evacuation.

The guide catheter can also be a double lumen extrusion of a single material, such as polyethylene. FIG. 4 is a cross sectional view of such a guide catheter 110a, comprising a first lumen 122 and a second lumen 124, as above. No braid is provided in this embodiment.

Figure 6:
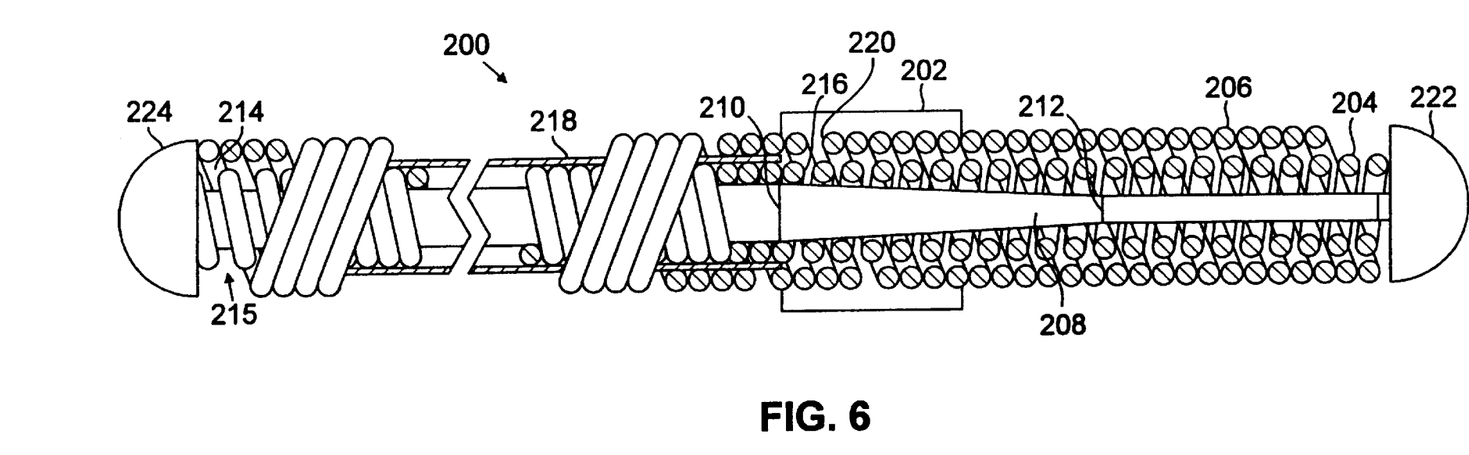
FIG. 6 is a partially sectioned view of a guide wire for use in the present invention.

FIG. 6 is a partially sectioned view of a guide wire 200 with an occlusion balloon 202, which can be used in the systems and methods of the present invention. The guide wire 200 preferably comprises an inner coil 204 and an outer coil 206, wound with opposite pitch, for improved torqueability and pushability. To further improve force transmission, the interior of the guide wire 200 preferably contains a solid core wire 208 having a constant diameter along substantially its entire length. The solid core wire 208 runs the entire length of the lumen of the inner coil 204. The handling characteristics of the guide wire 200 are preferably further improved by tapering the solid core wire 208 from point 210, which is about 5 cm from the distal tip of the solid core wire 208, to point 212, which is about 2 cm from the distal tip.

The inner coil 204 is preferably a spring coil of stainless steel wire having a unifilar or multifilar configuration which is close wound to near the diameter of point 210. A flexible sheath 218 preferably covers the inner coil 204 at the end of the guide wire 200 to near point 210. The sheath 218 is preferably a thin non-porous polymer, silicone rubber or polytetrafluoroethylene (PTFE) sleeve. The flexible sheath 218 ensures that pressure is maintained from a standard Touhy-Borst or other such connector, as shown in FIG. 1, to the infusion region 216.

The outer layer of the guide wire 200 comprises the outer coil 206, which is also preferably a quadrifilar stainless steel coil. It is preferably wound in an opposite pitch to the pitch of the inner coil 204, to improve the torque transmission characteristics of the guide wire 200. The outer coil 206 is also closely wound between the standard Touhy-Borst or other connector and the distal end of the guide wire, beginning at point 210. Semi-hemispherical welds 222, 224 fixedly attach the outer coil 206, inner coil 204, and solid core wire 208 at their distal and proximal ends, respectively.

The guide wire 200 of FIG. 6 can have an outer diameter of greater than about 0.022 inches. The guide wire 200 of FIG. 6 and other guide wires which can be used in the present invention are disclosed in U.S. Pat. No. 5,376,083, and are available from Lake Region Manufacturing Co., Inc., for example. An occlusion balloon 202 can be added to other commercial infusion guide wires, as well.

The proximal end 214 of the inner coil 204 and the proximal end 215 of the outer coil 206 are spaced to define an infusion region to permit infusion of a pressurized fluid from the inflation/deflation unit 358, shown in FIG. 1, into the guide wire 200, to inflate the occlusion balloon 202. A portion 216 of the inner coil 204 distal to point 210 of the inner coil 204 and a corresponding portion 220 of the outer coil 206 are similarly spaced to enable the infused fluid to exit the wire 200, to inflate the balloon 202. The balloon 202 is attached to the outer coil 206 of the guide wire 200, over the region, by adhesive. The occlusion balloon 202 can be any one of the materials discussed above with respect to the guide catheter 110. The outer diameter of the occlusion balloon 202 when fully inflated should be sufficiently greater than the diameter of the vessel that the balloon sufficiently bears against the vessel walls to prevent the passage of materials distal to the occlusion balloon 202, under pressure.

As above, in a deep vein with a diameter of about 6.0 mm, the fully inflated occlusion balloon preferably has a diameter of about 6.1 mm and a length of about 1–2 cm.

Additional regions of separation between the windings of the inner coil 204 and the outer coil 206 can also be provided proximal to the occlusion balloon 202 to enable the infusion of a lytic agent. The lytic agent can both inflate the occlusion balloon 202 and seep out of the guide wire 200.

Figure 7A:
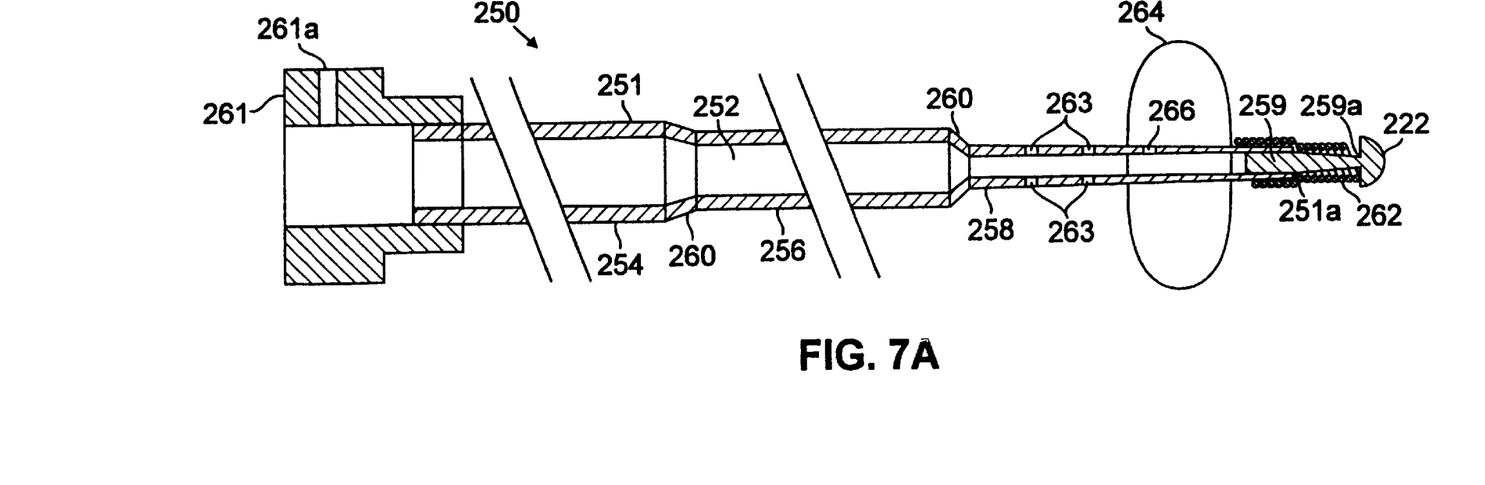
FIGS. 7A–7C are cross sectional views of alternative embodiments of the guide wire for use in the present invention.

FIG. 7A is an alternative guide wire 250 for use in the present invention. The guide wire 250 comprises a hollow wire 251 of superelastic nickel titanium with a central lumen 252. The proximal portion of the guide wire 250 must have sufficient rigidity for forces exerted on the proximal end, such as a forward force to advance the wire or a rotational force to turn the wire, to be sufficiently translated to the distal portion. The intermediate and distal portion of the guide wire 250, however, must also be soft enough to follow the turns of the vasculature and not damage tissue. Decreasing the outer diameter of a portion of the wire 251 of superelastic nickel titanium decreases its rigidity. The wire, therefore, comprises at least two sections of decreasing outer diameter.

In the embodiment of FIG. 7A, the guide wire 250 comprises a proximal portion 254, which preferably has an outer diameter of about 0.018 inches, an intermediate portion 256, which preferably has an outer diameter of about 0.015 inches and a distal portion 258, which preferably has an outer diameter of about 0.012 inches. Additional portions can be provided if desired. Tapered sections 260 separate each portion. The inner diameter of the proximal section 254 is about 0.015 inches, the inner diameter of the intermediate portion 256 is about 0.012 inches and the inner diameter of the distal portion 258 is about 0.009 inches. In a guide wire 250 with a length of about 180 cm, for example, the proximal portion 254 of the wire 250 can have a length of about 110 cm, the intermediate portion 256 can have a length of about 54.5 cm and the distal portion 258 can have a length of about 15.5 cm. The coil 262 can extend about 2–3 cm from the tip of the distal portion.

A solid rod or core 259 of stainless steel or tungsten, for example, is inserted into the lumen 252 of the distal portion 258 to seal the distal end of the wire 250. It can be soldered or adhered in place. Stainless steel grades 304 or 306 may be used, for example. The rod 259 preferably extends out of the lumen 252, beyond the distal tip 251a of the nickel titanium wire 251. The portion of the rod 259 extending from the lumen 252 is preferably tapered towards its distal end, to increase its flexibility. The portion of the rod 259 within the lumen 252 can have a diameter of about 0.008 inches, which can decrease to about 0.003 inches proximate its distal end 259a, for example. A semi-hemispherical weld 223 is preferably formed at the distal end 259a of the rod 259 by melting the tip of the rod 259 back in a plasma weld, for example, to protect tissue during advancement of the guide wire 250.

A wire coil 262 of tungsten or platinum, for example, is also preferably attached to the distal portion 250 and to the rod 259 to soften the distal tip of the guide wire 250 to protect tissue. In addition, the tungsten or platinum coil 262 is radiopaque, enabling tracking of the distal tip of the guide wire on a fluoroscope. The coil can be soldered or attached to the distal portion 250 by an adhesive. The coil 262 preferably extends about 2–3 cm from the tip 251a of the distal portion 258. The rod 259 preferably extends out the lumen 252 of the distal portion 258, to support the coil, as shown in FIG. 7A. A doctor can bend the coil 262 and rod 259 prior to a procedure, to ease the advance of the guide wire 250 to the desired site. Alternatively, the distal portion 258 of the guide wire 250 may be heat treated to remove its superelastic, shape memory properties, as is known in the art, so that a doctor can bend the distal portion 258 of the guide wire 250.

An occlusion balloon 264 is preferably provided in the distal portion 258 of the guide wire 250. A port 266 is provided through the wall of the distal portion 258, to provide fluid communication between the central lumen 252 and the region encompassed by the occlusion balloon 264. The occlusion balloon 264 can be any of the materials discussed above with respect to the guide catheter 110. The occlusion balloon 264 can be attached to the guide wire 250 by an adhesive. Cyanoacrylic adhesives, ultraviolet activated adhesives or epoxies may be used, for example. Preferably, the balloon inflation port 266 has a diameter of at least about 0.005 inches. Inflation fluid can be provided to the lumen 252 by a suitable connector 261, as is known in the art.

Lytic agents can also be delivered through this guide wire by providing small ports 263, shown in FIG. 7A, proximal to the occlusion balloon 264. The lytic agent can be used to inflate the balloon, and will seep out of the ports 263. The optional lytic agent delivery ports 263 preferably have a diameter of about 0.001–0.004 inches. If lytic agent is delivered through the guide wire 250, the infusion catheter 300 is not required.

Figure 7B:
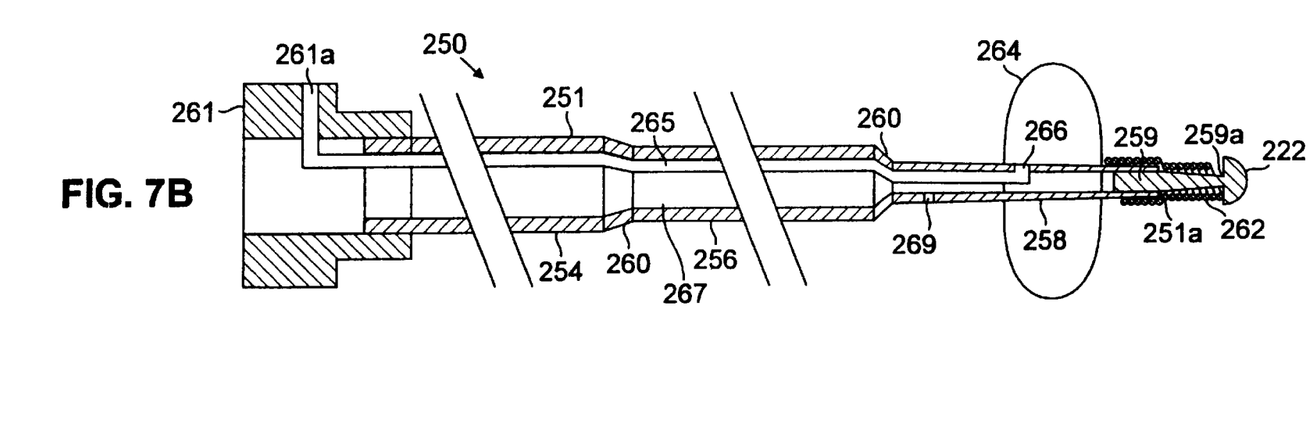

FIG. 7B is an alternative embodiment of the guide wire 250, wherein inflation fluid can be provided to the occlusion balloon through a plastic tube 265 attached to the wall of the central lumen 252. A port 261a can be provided in the connector 261 to provide the inflation fluid. The tube 265 can be adhered in place. This embodiment can also be used to deliver a lytic agent through connector 261, into the lumen 252, and out through the optional ports 269.

Figure 7C:
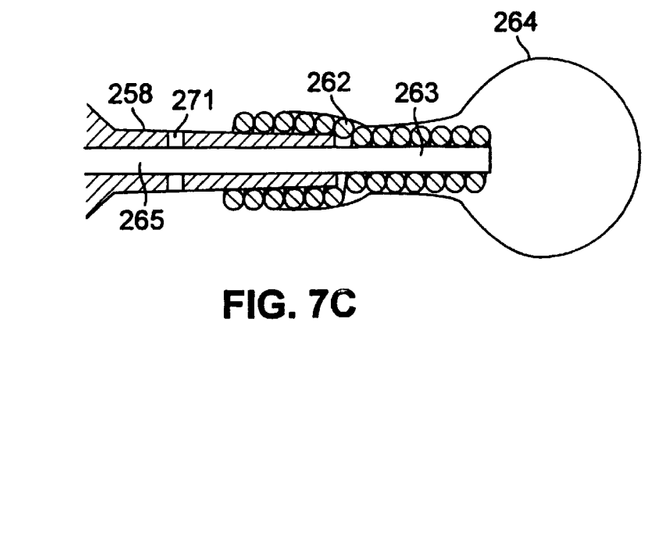

The occlusion balloon 264 can also be attached to the distal tip of the guide wire 200, over the coil 262, as shown in FIG. 7C. The coil 262 defines a hollow center 263, which provides fluid communication between the central lumen 265 of the wire 250 and the balloon 264. The occlusion balloon 264 can also be attached to the coil 262 by an adhesive. This embodiment can also be used to deliver a lytic agent by providing small ports 271 through the wall of the distal portion 258, proximal to the occlusion balloon 264. As discussed above, the lytic agent can both inflate the balloon through the central lumen 252 and, when the balloon is inflated, seep out of the ports 271.

The superelastic nickel titanium wire is preferably about 50% nickel, 50% titanium, such as Nitinol®, available from Raychem, Corporation, Menlo Park, Calif., for example. Other elements, such as cobalt, vanadium and copper, for example, may be included, as well. The guide wire 250 of nickel titanium with decreasing outer diameters is preferably manufactured in a metal drawing process. Suitably shaped wire is available from Nitinol Devices and Components, Inc., Freemont, Calif., and Euroflex, Germany. The wire can also be ground to the desired outer diameters by a centerless grinder, as is known in the art.

The guide wires 250 of FIGS. 7A–7C, are disclosed in U.S. Pat. No. 5,776,100, which is incorporate by reference herein.

Figure 8:
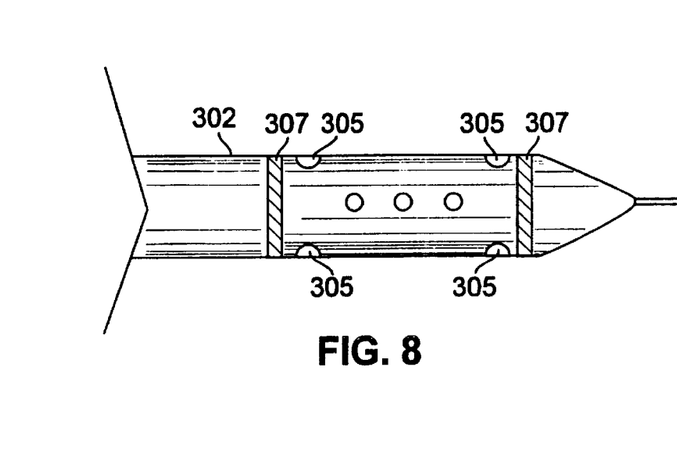
FIG. 8 is a side view of an infusion catheter for use in the present invention.
Figure 9:
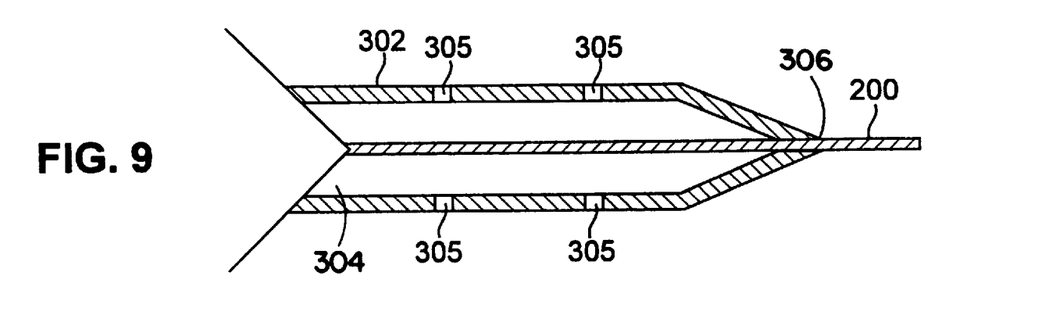
FIG. 9 is a cross sectional view of the infusion catheter of FIG. 8 through line 9—9.

FIGS. 8–9 are side and cross sectional views of an infusion catheter 300 which can be used in the systems and methods of the present invention. The cross sectional view of FIG. 9 is along the longitudinal axis of infusion catheter 300 in FIG. 8. The infusion catheter 300 typically comprises a shaft 302 with a central lumen 304 extending longitudinally through it. At least one port 305 is provided in the distal portion of the shaft to enable drugs or other agents injected through the infusion lumen 304, to exit the shaft. Ten ports are preferably provided, each with a diameter of about 0.015 inches, distributed around the shaft, along a length of about 1 inch. The distal portion of the infusion catheter 300 preferably tapers to a small opening 306, which has a diameter slightly smaller than the outer diameter of the guide wire 200, 250, such that the guide wire 200, 250 essentially seals the opening, preventing the passage of fluid.

The outer diameter of the infusion catheter 300 for use with the guide catheter 110 described above, is preferably about 0.050 inches. A larger infusion catheter 300 can be used if the corresponding guide wire/infusion catheter lumen 124 is larger. As mentioned above, however, a smaller diameter infusion catheter 200 is preferred to ease aspiration.

Commercially available infusion catheters can be used. One such commercially available infusion catheter is a Tracker from Target Therapeutics, Inc., Calif. The Tracker 18 or Tracker 25 can be used with guide wires with outer diameters of 0.018 inches or 0.025 inches, respectively. One or more radiopaque bands 307 of gold or tantalum, for example, can be provided for monitoring the position of the catheter 300 on a fluoroscope.

Returning to FIG. 1, at the proximal end of the system, the proximal portion of the guide wire 200, 250 and the second, inflation lumen 124 of the guide catheter 110 are each coupled to the balloon inflation/deflation unit 358. The infusion lumen 302 of the infusion catheter is coupled to the pump 354. A drip 357 containing the drug or lytic agent, such as urokinase, streptokinase or rTPA, or any other drug or lytic agent which can dissolve a thrombus, may be provided between the pump 354 and the infusion lumen 302. The first lumen 122 of the guide catheter 110 is preferably coupled to the pump 354 through the thrombus filter 352 and the saline reservoir 356 such that the lytic agent evacuated from the region proximal to the thrombus can be reused. If a third lumen is provided in the guide catheter 110 for evacuation, it would be connected to the filter 352 instead of the first lumen 122.

The pump 354 can be a roller pump which operates at 600 RPM. The MasterFlex® available from Cole-Palmer, Vernon Hills, Ill., and Baxter Scientific Products, McGraw Park, Ill., may be used, for example. The roller pump is arranged to deliver up to 300 millimeters per minute. Instead of providing a drip, the drug or lytic agent can be mixed in the saline reservoir 356 in the desired concentration, prior to the start of the procedure.

Figure 10:
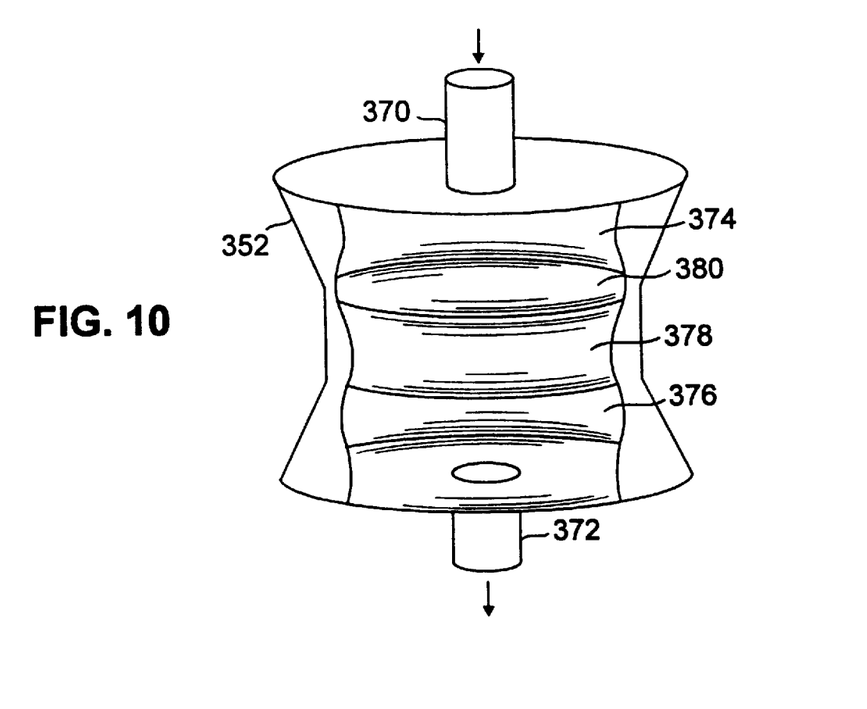
FIG. 10 is a partially sectioned view of a filter for use in the present invention.

FIG. 10 is a partial, cutaway view of an example of a thrombus filter 352 which can be used in the systems and methods of the present invention. The thrombus filter 352 can comprise an inlet 370 from the first lumen 122 of the guide catheter 110, an outlet 372 to the saline reservoir 356, first and second chambers 374, 376 and filtration material 378 between the first and second chambers. The filtration material 378 can be any biocompatible filtration material with a pore size of about 20–200 microns. The filtration material 378 can be a woven polymer such as polypropylene, PTFE or heparinized nylon or polyester, for example. Spectra/Mesh® Teflon® filters with a mesh opening of about 70–105 microns, an open area of about 22–34% and a thickness of about 158–170 microns, or Spectra/Mesh® polypropylene filters with a mesh opening of about 105–149 microns, an open area of about 26–34% and a thickness of about 212–193 microns, available from Spectrum® Medical Industries, Inc., Houston, Tex., can be used, for example. The filter can be contained in a Nalgene™ PSF filter holder with receiver, available from Nalge Company Inc., in Rochester, N.Y.

Material evacuated from the region proximal to the thrombus through the guide catheter 110 enters the first chamber 374 of the thrombus filter 352 through the inlet 370. The material fills the first chamber 334 and seeps through the filtration material 378. The filtered material collects in the second chamber 376 and exits through the outlet 372. The filtration material 378 removes thrombolytic material, and other such material which could clog the infusion pump 354. It also prevents thrombolytic material from being returned to the vein along with the recycled lytic agent, through the infusion catheter 300.

The system breaks up and dissolves a thrombus, such as the thrombus 360 in FIG. 1, by forcing a drug or lytic agent delivered distal to the thrombus 360 by the infusion catheter 300, through the thrombus 360, by creating a region of high pressure distal to the thrombus 360. As the drug or lytic agent is forced through the thrombus, the thrombus dissolves.

In a procedure in accordance with the present invention, a guide wire, such as the guide wire 200 or 250, is first inserted into the femoral vein, advanced over the femoral arch 364, and into the opposite femoral vein, through the thrombus 360. The distal tip of the guide wire 200, 250 can be advanced about 1–5 cm past the thrombus 360, for example. Then, the guide catheter 110 is advanced over the guide wire 200, 250 to a position proximal to the thrombus. The infusion catheter 300 is then inserted over the guide wire 200, 250 through the first lumen 122 of the guide catheter 110 and through the thrombus 360 such that its infusion port or ports 304 are distal to the thrombus 360. The positions of the guide wire 200, 250, guide catheter 110 and infusion catheter 300 can be monitored on a fluoroscope, as is known in the art. When the guide catheter 110, guide wire 200, 250 and infusion catheter 300 are properly positioned, the occlusion balloons 114 and 202 can be inflated by the balloon inflation/deflation units 358a, 358b, or by syringes, as is known in the art. It may be desirable to inflate the occlusion balloon 114 of the guide catheter 110 before the infusion catheter is advanced through the thrombus 360.

Inflation of an occlusion balloon, such as the balloon 202, distal to the thrombus, isolates a region 361. Inflation of another occlusion balloon, such as balloon 114, isolates a region 363 proximal to the thrombus 360. Drug or lytic agent is then delivered into the distal region 361, preferably at a pressure of about 0.5–2.0 atmospheres. Pressures of up to about two atmospheres are believed to be sufficient to force the lytic agent through the thrombus, into the proximal region 363, without damaging the venous tissue. As the lytic agent is forced through the thrombus 360, the agent, as well as broken or dissolved portions of the thrombus 362 and blood, are evacuated through the first lumen 122 of the guide catheter 110 or through an optional third lumen 126.

Since the evacuated lytic agent is filtered of thrombolytic material, it can be infused back into the distal isolated region. A saline reservoir 356 is preferably provided between the filter 352 and the infusion pump 354, to dilute the evacuated filtered material. A 359 is preferably provided to heat the saline and lytic agent to between about 42°–45° C. It has been found that heating the lytic agent speeds the dissolution of the thrombus. Recycling of the lytic agent decreases the amount of drug or lytic agent needed in the procedure, lowering its cost.

The procedure can continue until the thrombus 362 is completely removed. Preferably, the region between the occlusion balloons 202, 114 is flushed with saline prior to conclusion of the procedure to remove any remaining vestiges of thrombolytic material. The procedure can continue for five minutes up to several hours.

Figure 11:
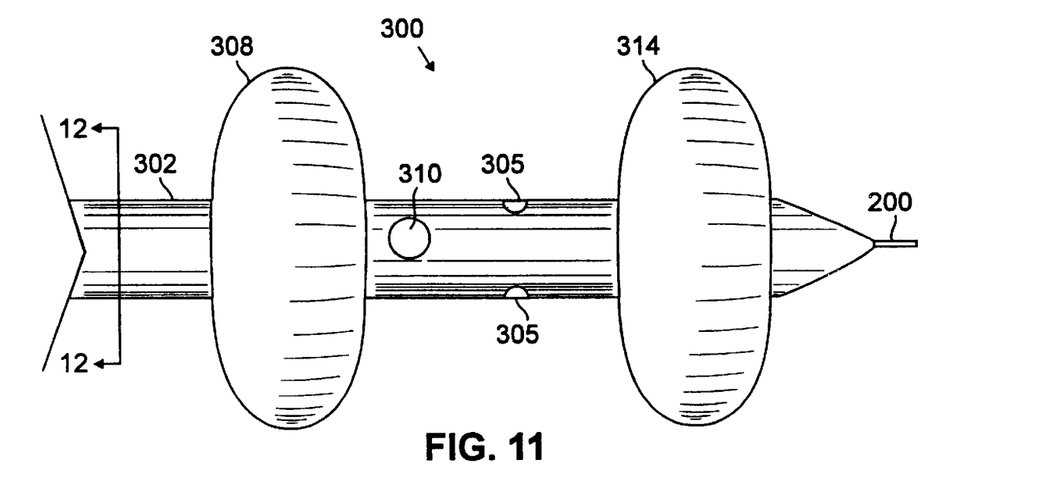
FIG. 11 is a side view of an alternative infusion catheter in accordance with another embodiment of the invention.
Figure 12:
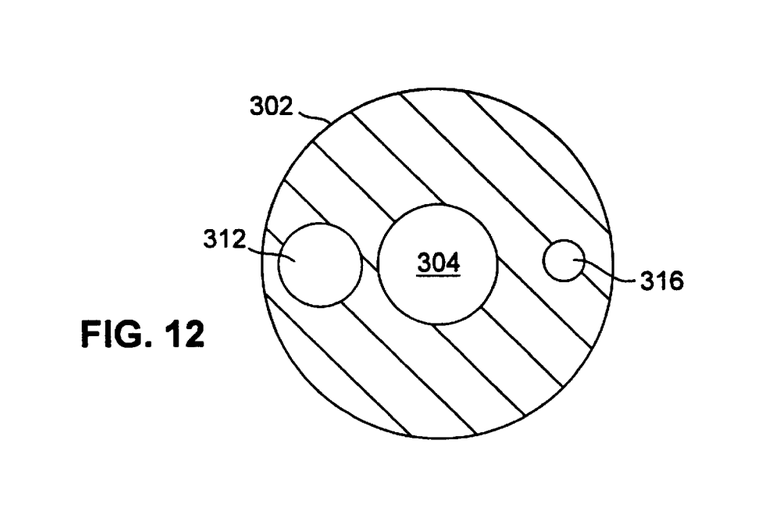
FIG. 12 is a cross sectional view of the infusion catheter of FIG. 11, through line 12—12.

It is preferred that the guide catheter 110 and guide wire 200 have their own occlusion balloons so that the guide catheter 110, guide wire 200 and infusion catheter 300 can be moved and positioned independently of each other. Instead of providing an occlusion balloon 114 on the guide catheter 110, however, a proximal occlusion balloon 308 can be provided on the infusion catheter 300, as shown in FIG. 11. Similarly, instead of providing an occlusion balloon on the guide wire 200, 250, a distal occlusion balloon 314 can be provided on the infusion catheter 300, also as shown in FIG. 11. An additional lumen 316 would then be provided in the infusion catheter 300 for inflation of the balloon 308, as shown in the cross sectional view of FIG. 12. If the proximal occlusion balloon is included on the infusion catheter 300, an evacuation port 310 and an evacuation lumen 312 would then preferably be provided in the infusion catheter. While FIG. 11 shows both the proximal and distal occlusion balloons 304, 308, only one or the other can be provided if desired.

After application of the lytic agent for a sufficient amount of time, the region can be flushed with saline to remove any remaining thrombolytic material. A further option is to deliver an anticoagulant such as heparin or an antiproliferative such as dexamethasone into the occluded region through the same system to prevent restensosis. Examples of other anticoagulants and antiproliferatives are listed below.

Deep vein thrombosis can also be treated in accordance with the present invention by insertion of the system through the pedis dorsal vein of the foot. For a long clot, a dual approach through the femoral vein and pedis dorsal vein concurrently, may be useful to break up and dissolve the clot progressively from both ends.

The system of the present invention is preferably provided in a kit, preferably comprising the guide catheter 110 with the occlusion balloon 114, the guide wire 200 or 250 and occlusion balloon 202 or 264, and infusion catheter 300, in sterile shrink wrapping. If drugs or lytic agents can be delivered through the guide wire, the infusion catheter is not required in the kit. If the infusion catheter includes proximal and/or distal occlusion balloons, then the guide wire and guide catheter in the kit would not need occlusion balloons.

While described with respect to a drug or lytic agents such as urokinase, streptokinase and rTPA, other drugs or agents, including those listed below, may be used.

The present invention can be used to treat thrombosis in any blood vessel of the body. It can also be used to drive appropriate drugs or agents through other types of blockages or occlusions, such as tumors, in other vessels or chambers of the body, such as the urethra, bladder, prostate, rectum, bile duct, pancreatic duct, kidney and central nervous system, such as along the spinal column.

It could also be advantageous to deliver drugs or other agents into occluded regions of a lumen, vessel or cavity, even if there are no blockages. For example, drugs or agents, such as anticoagulants and antiproliferatives can be delivered to the site of a percutaneous transluminal coronary angioplasty (PCTA) or percutaneous transluminal angioplasty (PTA) procedure to prevent restenosis. The delivered drug or agent can be delivered under pressure, evacuated and recycled, if desired, as described above. Suitable anticoagulants include heparin, hirudin, hirulog, hirugen, activated and non-activated protein C, synthetic or naturally occurring antagonists of thrombin, and Factor Xa, or other activated or non-activated coagulation protease inhibitors and coagulation factors, e.g., FIX, FVIII, FV, FVIIa and tissue factor, for example.

Antiproliferatives include dexamethasone, growth factor, a growth factor inhibitor, growth factor receptor antagonist, transcriptional repressor, translational repressor, antisense DNA, antisense RNA, replication inhibitor, inhibitory antibodies, antibodies directed against growth factors or their receptors, bifunctional molecules comprising a growth factor and a cytotoxin, bifunctional molecules comprising an antibody and a cytotoxin, for example.

Polaxymer 188, another antiproliferative, can also be delivered in accordance with the present invention to pave or line the walls of an artery to prevent smooth muscle growth.

The agent delivered by the systems and methods of the present invention can also be a vasodilator, such as nitroglycerin, nitroprusside or other nitric oxide liberators. The vasodilator can also include other suitable vasoactive agents such as beta receptor blocking drugs, inhibitors of intra-cellular calcium transport, prostaglandins, thromboxane antagonists, and the like.

Other drugs or agents which can be delivered include substances which inhibit platelet deposition and thrombus formation or promote thrombolysis and thrombus dissolution, such as plasmin, tissue plasminogen activator (tPA), single chain prourokinase (scuPA), prostaglandins, cyclooxygenase inhibitors, phosphodiesterase inhibitors, thromboxane synthetase inhibitors; antagonists of glycoprotein receptors including (GP) Ib, GP IIb/IIIa, antagonists of collagen receptors, and antagonists of platelet thrombin receptors, for example.

Alternatively, the drugs or agents delivered by the systems and methods of the present invention can directly affect platelet metabolic function. Examples of such substances include prostaglandins, cyclooxygenase inhibitors, phosphodiesterase or thromboxane synthetase inhibitors, inhibitors of calcium transport, or elevators of cyclic adenosine monophosphate (cyclic AMP).

The above embodiments are examples of systems and methods of the present invention, which are defined in the following claims.

We claim:

1. A system for treating a blockage in a lumen, vessel or cavity comprising:

means for delivering a drug or other agent to a first region proximate the blockage, means for forcing the drug or other agent from the first region through the thrombus, comprising a pump in fluid communication with the first region which delivers drugs or other agents into the first region under pressure;

means for occluding the region; and a filter coupled to the means for delivering such that filtered material comprising filtered drug or other agent is delivered to the first region.

2. A system for treating thrombosis comprising:

at least one inflation/deflation unit;

a first occlusion balloon coupled to the inflation/deflation unit, such that the first occlusion balloon can isolate a region distal to a thrombus;

a second occlusion balloon coupled to the inflation/deflation unit, such that the second occlusion balloon can isolate a second region proximal to the thrombus;

a pump;

a first lumen coupled to the pump and the first region, wherein a drug or lytic agent can be infused into the first region through the first lumen under pressure by the pump, to force the drug or other agent through the thrombus;

a second lumen coupled to the pump and the second region wherein the material can be evacuated from the second region; and a filter between the second lumen and the pump, such that material evacuated from the second region is filtered prior to infusion into the first region through the first lumen.

3. The system of claim 2, further comprising a guide catheter, wherein the first occlusion balloon is part of the guide catheter.

4. The system of claim 2, further comprising an infusion catheter, wherein the first occlusion balloon is part of the infusion catheter.

5. The system of claim 2, further comprising an infusion catheter, wherein the first lumen is part of the infusion catheter.

6. The system of claim 2, further comprising a guide wire, wherein the first lumen is part of the guide wire.

7. The system of claim 2, further comprising an infusion catheter, wherein the second occlusion balloon is coupled to the infusion catheter.

8. The system of claim 2, further comprising a guide wire, wherein the second occlusion balloon is coupled to the guide wire.

* * * * *